United States Patent [19]

Kennerley

[11] 3,969,500

[45] July 13, 1976

[54] SHAMPOO CONTAINING A WATER-SOLUBLE LINEAR CARBOXYLIC POLYMER

[75] Inventor: Malcolm George Kennerley, Edwalton, England

[73] Assignee: Lever Brothers Company, New York, N.Y.

[22] Filed: Sept. 3, 1974

[21] Appl. No.: 502,696

Related U.S. Application Data

[63] Continuation of Ser. No. 336,093, Feb. 26, 1973, abandoned.

[30] Foreign Application Priority Data

Mar. 3, 1972 United Kingdom............... 9969/72

[52] U.S. Cl............................ 424/10; 252/DIG. 2; 252/DIG. 3; 252/DIG. 13; 252/549; 252/550; 252/551; 252/554; 252/558; 424/DIG. 2; 424/71; 424/78; 424/81
[51] Int. Cl.².......................................... A61K 7/06
[58] Field of Search................. 424/70, DIG. 2, 71, 424/78, 81; 252/DIG. 2, DIG. 3, DIG. 13, 549, 550, 551, 554, 558

[56] References Cited
UNITED STATES PATENTS

| | | | |
|---|---|---|---|
| 2,806,842 | 9/1957 | Gerecht et al. | 424/70 X |
| 3,322,676 | 5/1967 | Hiestand | 424/70 X |
| 3,684,777 | 8/1972 | Field et al. | 424/70 X |
| 3,708,426 | 1/1973 | Schrader | 424/70 X |
| 3,723,375 | 3/1973 | Field et al. | 424/70 X |

Primary Examiner—Albert T. Meyers
Assistant Examiner—Vera C. Clarke
Attorney, Agent, or Firm—Arnold Grant

[57] ABSTRACT

The invention concerns a shampoo which improves the lustre and combability of the hair and which comprises an aqueous solution of a non-soap synthetic anionic detergent and from 0.05 to 5% by weight of certain water-soluble carboxylic linear polymers, preferably poly(methacrylic acid) of molecular weight between 10,000 and 100,000.

1 Claim, No Drawings

SHAMPOO CONTAINING A WATER-SOLUBLE LINEAR CARBOXYLIC POLYMER

This is a continuation of application Ser. No. 336,093, filed Feb. 26, 1973, now abandoned.

This invention relates to hair preparations, more particularly to shampoos.

It is desirable that after shampooing, the hair should have a healthy, naturally shiny appearance and good combability.

We have discovered that certain water-soluble carboxylic polymers are adsorbed onto the hair in substantial amounts from aqueous solutions and that the adsorbed polymer film imparts a shine to the hair and improves its combability. Furthermore, it has been found that this adsorption of polymer also takes place in the presence of anionic detergents with which the polymer, being itself anionic, is compatible. These findings have enabled us to formulate improved aqueous shampoo compositions which leave the hair with an enhanced lustre and easier to comb after the shampooing operation.

Accordingly the present invention provides a shampoo comprising an aqueous solution of a non-soap synthetic anionic organic detergent and from 0.05 to 5% by weight of a water-soluble carboxylic linear polymer which contains carboxylic acid units of the general formula:

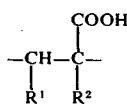

where $R^1$ is H, $CH_3$ or COOH and $R^2$ is H, $CH_3$ or $CH_2COOH$; which polymer may also comprise units derived from a monoethylenically unsaturated compound, in particular units of the general formula:

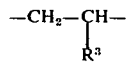

where $R^3$ is H, $C_6H_5$, $OOC.CH_3$, $OCH_3$ or $CONH_2$. The said polymer may be present in the shampoo either in its acid form or as a water-soluble salt thereof.

Thus, the polymers which may be included in the shampoo of the invention include polymers of acrylic acid, methacrylic acid, crotonic acid, itaconic acid and maleic acid, and their copolymers with a monoethylenically unsaturated monomer, especially ethylene, vinyl benzene, vinyl acetate, vinyl methyl ether and acrylamide.

Preferred shampoos in accordance with the invention are those comprising a water-soluble polymer in which $R^1$ = H or COOH, $R^2$ = H or $CH_3$ and, if present, $R^3$ = H or $OCH_3$, and particularly the polymers of the following general formula:

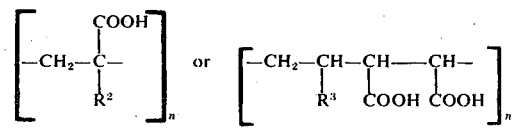

where $R^2$ is H or $CH_3$, $R^3$ is H or $OCH_3$ and $n$ indicates the degree of polymerization, and water-soluble derivatives of these polymers.

The most preferred carboxylic polymers include those obtained by the hydrolysis of poly(ethylene/maleic anhydride) and poly(methyl vinyl ether/maleic anhydride), and their water-soluble salts, with the best results being obtained by using poly(methacrylic acid) and its water-soluble salts.

Poly(methacrylic acid) is usually obtained from the corresponding alkyl ester. It is not essential for the purpose of this invention that the ester be completely hydrolyzed. Sufficient hydrolysis is necessary to impart a satisfactory degree of water-solubility although substantially complete conversion to the acid form is preferred since such a form permits one to formulate shampoos which are clear in appearance.

As stated above, the carboxylic polymer may be employed in the form of a water-soluble salt. Any water-soluble salt may be used. Examples of such salts are the alkali metal, alkaline-earth metal, ammonium and amine salts. Specific illustrations of these are the sodium, potassium, calcium, magnesium, monoethanolamine, diethanolamine, and triethanolamine salts.

The polymers used in this invention are linear and are not subjected to cross-linking, since then the polymers become water-insoluble. It is known to use cross-linked polymers in shampoos as thickening agents.

The carboxylic polymers employed in compositions of this invention being water-soluble will usually have molecular weights in the range 1,000 to 500,000. Preferably polymers are used of a molecular weight of 10,000 to 100,000.

Especially preferred are those water-soluble carboxylic polymers which have relatively little thickening action (i.e. those of which a 2% aqueous solution has a viscosity of less than 50 centipoises, and preferably less than 30 centipoises, at 25°C). The use of these polymers permits one to obtain shampoos having a wide range of viscosities ranging from very low viscosity shampoos (200 centipoises or less) to viscous shampoos (1,000 centipoises or more), since if a viscous product is desired this can be achieved through the use of conventional thickening agents. The following Table 1 illustrates the influence of concentration on the viscosity of an aqueous solution of a typical commercially available poly(methacrylic acid) salt and of water-soluble polymers obtained by hydrolysis of two commercially available polymers containing carboxylic anhydride groups.

TABLE 1

| Polymer | Concentration Weight % | Viscosity Centipoises |
|---|---|---|
| Potassium polymethacrylate | 5.8 | 4.4 |
| Potassium polymethacrylate | 1.2 | 2.7 |
| Potassium polymethacrylate | 0.1 | 1.6 |
| Hydrolyzed poly(methyl vinyl ether/maleic anhydride) | 5.0 | 3.0 |
| Hydrolyzed poly(methyl vinyl ether/maleic anhydride) | 1.0 | 1.6 |
| Hydrolyzed poly(ethylene/maleic anhydride) | 10.0 | 1.7 |
| Hydrolyzed poly(ethylene/maleic anhydride) | 1.0 | 1.1 |

Suitable amounts of the carboxylic polymer in the shampoo range from about 0.05 to about 5 percent, preferably from about 0.1 to about 2% by weight based on the total shampoo composition.

The anionic detergent can be any of those usually used in shampoos. Examples include alkyl sulphates, alkyl ether sulphates, alkyl sulphonates, alkyl benzene sulphonates, sulphosuccinates and the product, normally called olefin sulphonate, made by the sulphonation of random or alpha-olefins and neutralization and hydrolysis of the acid mix obtained. The concentration of the anionic detergent should be selected to give adequate cleansing and foaming. Typical amounts are, by weight, from 5 to 50 percent of the composition, preferably 8 to 30 percent.

The pH of the shampoo can be, if necessary by adjustment, from 3 to 10, preferably above 5. PH's within the range from 6 to 8 are particularly suitable. Th shampoo can contain any of the components usually used for shampoos, e.g. foam boosters, hydrotropes, nonionic detergents, proteins, herbs, opacifying agents, thickeners, colouring agents and perfumes.

The invention also relates to a process of treating hair particularly human hair which comprises treating the hair with a shampoo according to the invention.

The invention will now be illustrated with reference to various shampoo formulations which are given in Table 2.

poo (i.e. the shampoo without the carboxylic polymer but with the same pH). For each comparison six hair switches were chosen from a number of switches which had been shown by the goniophotometer to have similar gloss. Three hair switches were shampooed in a shampoo according to the invention and three switches were washed in the corresponding base shampoo. The switches were allowed to dry and then placed in the goniophotometer. The graph of the intensity of the reflected light against the detector angle was determined three times for each switch.

In Table 3 is given for each shampoo the difference ($\Delta G$) between the mean of the G values for hair treated with shampoo containing carboxylic polymer and the mean of the G values for hair treated with the base shampoo.

TABLE 3

| Shampoo | $\Delta G$ |
|---|---|
| I | +0.214 |
| II | +0.120 |
| III | +0.116 |
| IIIA | +0.032 |
| IIIB | +0.059 |
| IIIC | +0.236*  +0.285* |
| IV | +0.068*  +0.085* |

TABLE 2

| Ingredient | | | | Weight% | | | |
|---|---|---|---|---|---|---|---|
| Shampoo: | I | II | III | IV | V | VI |
| Monoethanolamine lauryl sulphate | 12.00 | 12.00 | — | — | — | — |
| Sodium lauryl ether sulphate | — | — | 12.00 | 12.00 | 12.00 | 12.00 |
| Poly(methacrylic acid) | 1.00 | — | 1.00 | 0.50 | 0.10 | — |
| Hydrolyzed poly(ethylene/maleic anhydride)[1] | — | 0.57 | — | — | — | — |
| Hydrolyzed poly(methyl vinyl ether/maleic anhydride)[2] | — | — | — | — | — | 0.56 |
| Lauric isopropanolamide | 1.00 | 1.00 | 1.00 | 1.00 | 1.00 | 1.00 |
| Colour, perfume, water | ←―――――――― to 100.00 ――――――――→ | | | | | |
| pH | 7.1 | 7.0 | 7.5 | 7.3 | 7.3 | 6.4 |

[1]Molecular weight about 17,000
[2]Molecular weight about 45,000

Together with the above shampoos, three other shampoos (IIIA, IIIB and IIIC) were prepared. These had the same composition as shampoo III but had a different pH. Shampoos IIIA, IIIB and IIIC had pHs of 3.2, 5.0 and 7.0, respectively.

The poly(methacrylic acid) in shampoo I was added in its acid form and had a molecular weight of 22,000. The poly (methacrylic acid) in shampoos III to V was added in the form of the potassium salt having a molecular weight of 70,000. The poly(ethylene/maleic anhydride) was one of which a 2% aqueous solution at 25°C had a viscosity of 2 cps and a 10% aqueous solution of the poly(methyl vinyl ether/maleic anhydride) had a viscosity at 25°C of 30 cps; these copolymers were hydrolyzed by dispersing them in water and heating at 80°C until the solution became clear.

In the experiments described below an evaluation of the gloss of the hair was made using a goniophotometer. This instrument consisted essentially of a fixed light source and a light detector moveable through a fixed angle. The detector received reflected light from a hair switch and a graph was obtained of the intensity of the reflected light against the detector angle. The graph obtained had the shape of a peak.

The ratio (G) of the height of the peak to its width at one quarter of that height is a measure of the gloss of the hair and tests have shown that this correlates well with the subjective appreciation of shine.

In the evaluation of the above shampoos, each shampoo was compared with the corresponding base sham-

| V | +0.234 |
|---|---|
| VI | +0.092 |

*Independent gloss tests

The standard error in all these results was 0.028G.

A value for $\Delta G$ of +0.184 corresponds to a difference in gloss such that 75 percent of a sample of people can notice the difference in gloss between hair switches.

These results indicate that the shampoos containing the several types of carboxyl-containing polymers are capable of improving gloss and that the gloss effect can be produced over a range of pH.

A further test involving shampoo IIIC was performed. This was a standard half head shampoo test carried out on 30 heads of which 15 heads had been permed within the previous 3 months and 15 heads were unpermed. One half of each head was treated with shampoo IIIC and the other half with base shampoo (i.e. the shampoo without the carboxylic polymer but with the same pH). After drying, the gloss of each half head was assessed by the operator (hairdresser). Out of the 30 heads, the shampoo containing carboxylic polymer was judged to give better gloss on 17 occasions, there were 8 no differences and 5 times the base shampoo was judged better for gloss. This result is significant at 1 in 100. Out of the 15 heads which had been permed in the previous three months, the shampoo containing carboxylic polymer was judged to give better gloss on 10 occasions, there were 4 judgements of no difference, and only 1 judgement that the base shampoo was superior for gloss. This result is signifiant at 1 in 1,000.

It was also noticed that the foam from the shampoo containing carboxylic polymer was creamier than that from the base, and that hair (especially the permed hair) treated with the shampoo containing carboxylic polymer was softer, smoother and in better condition than hair treated with the base shampoo. There was no evidence of polymer flaking from the hair treated with the shampoo containing the carboxylic polymer.

The improved ease of combing following treatment with a shampoo in accordance with the invention was demonstrated by the following experiment. The shampoo (VII) containing carboxylic polymer used in this experiment had the following formula:

| Shampoo VII | Weight % |
|---|---|
| Sodium lauryl ether sulphate | 14.00 |
| Lauric isopropanolamide | 1.00 |
| Poly(methacrylic acid)* | 1.00 |
| Colour, perfume, water | to 100.00 |

*as used in Shampoos III to V

The combing resistance of a pair of hair switches was measured after treatment with a base shampoo. The switches were then washed using shampoo VII and rinsed with water, after which the combing resistance was remeasured. This procedure was repeated using another pair of switches save that these switches were washed using shampoo A (i.e., shampoo VII from which the poly(methacrylic acid) had been omitted). Combing resistance measurements were made either on the wet hair directly after the shampooing and rinsing or after drying the hair. The combing resistance measurements were made using a comb fitted with a strain guage in such a way as to measure the force required to comb a hair switch.

In the case where the combing resistance of wet hair was measured, the base shampoo employed consisted of a 14% by weight aqueous solution of monoethanolamine lauryl sulphate and where the measurement was made on dry hair the base shampoo used consisted of a 14% by weight aqueous solution of sodium lauryl ether sulphate.

In the following Table 4 is given the average combing resistance of the hair switches after treatment with shampoos VII and A, respectively, expressed as a percentage of the average combing resistance of the hair switches after treatment with the respective base shampoo.

TABLE 4

| Shampoo | % Combing Resistance | |
|---|---|---|
| | Wet Hair | Dry Hair |
| VII | 102.3 | 82.3 |
| A | 123.4 | 103.2 |

It is clearly seen from these results that the inclusion of the carboxylic polymer in the shampoo resulted in an improvement in the ease of combing of hair washed with the shampoo.

What is claimed is:

1. A shampoo which improves the lustre and ease of combing of the hair comprising an aqueous solution having a pH value of from about 3 to about 10 of
   i. from about 5 to about 50% by weight of a non-soap synthetic anionic detergent selected from the group consisting of an alkyl sulphate, an alkyl ether sulphate, an alkyl sulphonate, an alkyl benzene sulphonate and a sulphosuccinate; and
   ii. from 0.05 to 5% by weight of a water soluble carboxylic linear polymer having a molecular weight of about 1,000 to about 500,000 which contains repeating carboxylic acid units selected from the formulae consisting of:

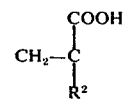

and

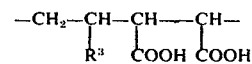

wherein $R^2$ is H or $CH_3$ and $R^3$ is H or $OCH_3$, or the water soluble salt thereof.

* * * * *